United States Patent [19]
Van Den Heuvel

[11] Patent Number: 5,503,161
[45] Date of Patent: Apr. 2, 1996

[54] UNIVERSAL MEDICAL INSTRUMENT BASED ON SPECTRUM ANALYSIS

[76] Inventor: Raymond C. Van Den Heuvel, 18618 Celtic St., Northridge, Calif. 91326

[21] Appl. No.: 143,456

[22] Filed: Oct. 25, 1993

[51] Int. Cl.$^6$ ................................................ A61B 7/00
[52] U.S. Cl. ............................................................ 128/773
[58] Field of Search .................................... 128/715, 773, 128/774, 687, 721

[56] References Cited

U.S. PATENT DOCUMENTS

| | | | |
|---|---|---|---|
| 4,008,711 | 2/1977 | Olinger et al. | 128/773 |
| 5,012,815 | 5/1991 | Bennett, Jr. et al. | 128/715 |
| 5,074,309 | 12/1991 | Gerdt | 128/715 |
| 5,301,679 | 4/1994 | Taylor | 128/773 |

Primary Examiner—George Manuel

[57] ABSTRACT

In a universal instrument for medical care a biocomputer is connected directly to the patient and uses sound and chemical spectrum analyzers to generate electronic signatures indicative of health conditions. The sound spectrum analyzer is an artificial cochlea that emulates a large number of tuned filters that operate in parallel and in real time. The chemical spectrum analyzer is a modified version of the well-known mass spectrometer. "Encyclopedic" knowledge and other computer aids are also included.

2 Claims, 1 Drawing Sheet

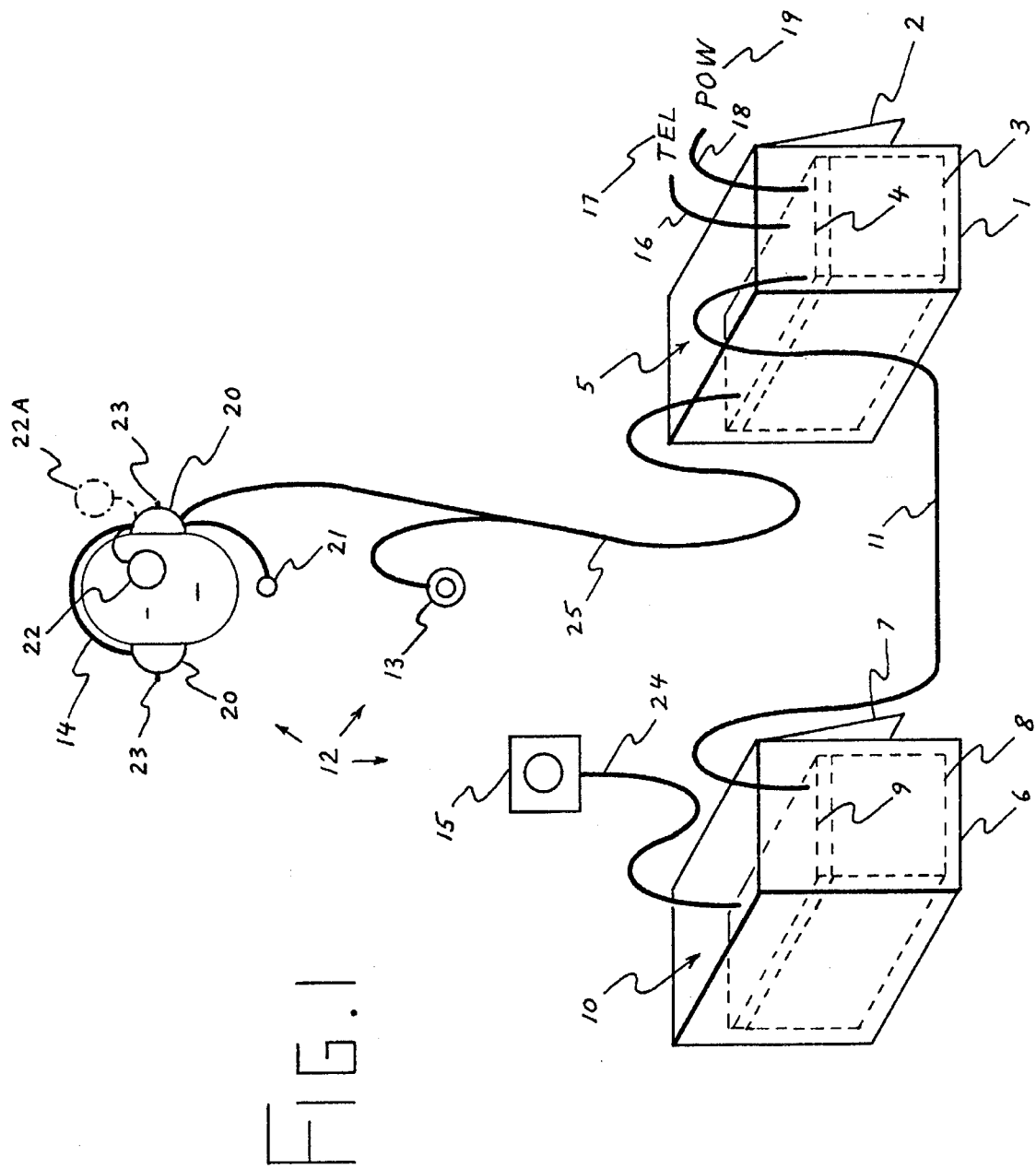

UNIVERSAL MEDICAL INSTRUMENT BASED ON SPECTRUM ANALYSIS

CROSS-REFERENCES by the same author

1. U.S. Pat. No. 4,649,506 (Mar. 10, 1987)—"Vector Generator Using Interpolative Analog Circuits."
2. U.S. Pat. No. 4,809,222 (Feb. 28, 1989)—"Associative and Organic Memory Circuits and Methods."
3. U.S. Pat. No. 4,984,176 (Jan. 8, 1991)—"VDH Biocomputer."
4. U.S. application Ser. No. 07/912,899 (filed Jul. 13, 1992)—"Multiprocessing Element for Computing Using Exact and Inexact Data."

REFERENCED DOCUMENTS

J. D. Andrade, "Improved Delivery and Reduced Costs Of Health Care Through Engineering: Discussion Meeting—Apr. 23–24, 1992, Washington, D.C.," *IEEE Engineering in Medicine and Biology*, pp. 38–41, June 1993.

John C. Wood, Andrew J. Buda, and Daniel T. Barry, "Time-Frequency Transforms: A New Approach to First Heart Sound Frequency Dynamics," *IEEE Transactions on Biomedical Engineering*, vol. 39, No. 7, pp. 730–740, July 1992.

Yasemin M. Akay, Metin Akay, Walter Welkowitz, John L. Semmlow and John B. Kostis, "Noninvasive Acoustical Detection of Coronary Artery Disease: A Comparative Study of Signal Processing Methods," *Transactions on Biomedical Engineering*, pp. 571–578, June 1993.

Yuan-Ting Zhang, Cyril Basil Frank, Rangaraj Mandayam Rangayyan and Gordon Douglas Bell, "A Comparative Study of Simultaneous Vibromyography with Active Human Ouadriceps," *IEEE Transactions on Biomedical Engineering*, vol. 39, No. 10, pp. 1045–1052, October 1992.

Arnon Cohen, "Signal Processing Methods for Upper Airway and Pulmonary Dysfunction Diagnosis," *IEEE Engineering in Medicine and Biology Magazine*, pp. 72–75, March 1990.

Ingvar Sodal and George Swanson, PH.D., "Making the mass spectrometer an efficient anesthetist's aide," *EMB Magazine*, March 1982.

Sateh M. Jalaleddine, Chriswell G. Hutchens, Robert D. Strattan and William A. Coberly, "ECG Data Compression Techniques—A Unified Approach," *IEEE Transactions on Biomedical Engineering*, vol. 37, No. 4, pp. 329–343, April 1990.

James W. Waite, "A Multirate Bank of Digital Bandpass Filters for Acoustic Applications," *Hewlett-Packard Journal*, pp. 73–81, April 1993.

BACKGROUND OF THE INVENTION

The cost of medical care is increasingly getting out of control due to a fragmentation of medical care brought about, in large part, by a proliferation of (expensive) medical tools and specialties. Furthermore each specialty is, more often than not, an outgrowth of an isolated technological solution (instrument or procedure.) A good beginning would be to change the focus of technology. This is in fact already happening.

Prior art and emerging trends are illustrated in the following articles. Note the increasing popularity of (frequency) spectrum analysis.

J. D. Andrade, "Improved Delivery and Reduced Costs Of Health Care Through Engineering: Discussion Meeting—Apr. 23–24, 1992, Washington, D.C.," *IEEE Engineering in Medicine and Biology*, pp. 38–41, June 1993. According to this autor cost savings could be provided by better information handling and record keeping, and by increasing the bedside or near bedside availability of tests and related information. Information and communications technologies and systems should be available to provide on-site information at the decision point. This information, together with available clinical practice guidelines and codification of diagnostic and therapeutic strategies, would permit more rapid and more effective on-site diagnosis. More effective and more remote noninvasive monitoring should be considered, including the opportunity for near continuous remote monitoring of at risk patients. Means to process and handle large volumes of information are needed, including neural networks, fuzzy logic, and expert systems. More effective education and training can be accomplished using the skills and techniques of the game and entertainment industry, particularly video, robotic, and virtual reality technologies.

John C. Wood, Andrew J. Buda, and Daniel T. Barry, "Time-Frequency Transforms: A New Approach to First Heart Sound Frequency Dynamics," *IEEE Transactions on Biomedical Engineering*, vol. 39, No. 7, pp. 730–740, July 1992. According to the authors the Binomial Transform provides much better resolution than the spectrograph or spectrogram, the two most common non-stationary signal analysis techniques. Previously, heart sound dynamic frequency analysis has primarily relied upon analog bandpass filtration methods such as the sound spectrograph. This method is time-consuming and requires expensive instrumentation. In addition, the overlapping filter passbands produce poor frequency resolution, particularly in the frequencies below 100 Hz.

Yasemin M. Akay, Metin Akay, Walter Welkowitz, John L. Semmlow and John B. Kostis, "Noninvasive Acoustical Detection of Coronary Artery Disease: A Comparative Study of Signal Processing Methods," *Transactions on Biomedical Engineering*, pp. 571–578, June 1993. The authors report that previous studies have indicated that heart sounds may contain information useful in the detection of occluded coronary arteries. In order to detect such sounds, recordings of diastolic heart sound segments were analyzed by using four signal processing techniques: the Fast Fourier Transform (FFT), the Autoregressive (AR), the Autoregressive Moving Average (ARMA), and the Minimum-Norm (Eigenvector) methods. To further enhance the diastolic heart sounds and reduce background noise, an Adaptive filter was used as a preprocessor. The results confirm that high-energy acoustic energy between 300 and 800 Hz is associated with coronary stenosis.

Yuan-Ting Zhang, Cyril Basil Frank, Rangaraj Mandayam Rangayyan and Gordon Douglas Bell, "A Comparative Study of Simultaneous Vibromyography with Active Human Quadriceps," *IEEE Transactions on Biomedicel Engineering*, vol. 39, No. 10, pp. 1045–1052, October 1992. Results of all these studies show that the VMG, as a direct mechanical index of muscular contraction, has potential as a noninvasive tool for studying the mechanical behavior of active skeletal muscles.

Arnon Cohen, "Signal Processing Methods for Upper Airway and Pulmonary Dysfunction Diagnosis," *IEEE Engineering in Medicine and Biology Magazine*, pp. 72–75, March 1990. According to this autor analysis of the acoustic characteristics of the thorax by sophisticated signal processing methods shows promise for assisting clinical diagnosis.

The technique is simple, quantitative, non-invasive, and objective. In some cases, especially in pediatrics, it closes a gap between the simple stethoscope and expensive invasive methods. This inexpensive implementation will allow the development of home care systems for the analysis and long term monitoring of, for example, snoring or asthmatic attacks. The application of modern sophisticated signal processing methods to auscultation may overcome the disadvantages of conventional auscultation and provide a simple, inexpensive, non-invasive, objective, and quantitative diagnostic tool. Simple microphone transducers are used.

Ingvar Sodal and George Swanson, PH.D., "Making the mass spectrometer an efficient anesthetist's aide," *EMB Magazine,* March 1982. The authors have developed a quadrupole mass spectrometer that is a miniature device and has promising implications for anesthetic gas monitoring, critical patient care and for respiratory research. It could serve as a rapid, multichannel gas analyzer in the physiology laboratory. It should lead to the development of better noninvasive measurements of cardiac output and lung tissue volume.

Sateh M. Jalaleddine, Chriswell G. Hutchens, Robert D. Strattan and William A. Coberly, "ECG Data Compression Techniques—A Unified Approach," *IEEE Transactions on Biomedical Engineering,* vol. 37, No. 4, pp. 329–343, April 1990. The transformation methods, briefly presented, include: Fourier, Walsh, and K-L transforms. Data compression by the transformation or the direct data compression methods contains transformed or actual data from the original signal. Whereby, the original data are reconstructed by an inverse process. The objective . . . is to preserve the minimum essential information required to ensure reliable clinical diagnosis for a specific ECG lead(s) application. The result of this standardization . . . will include . . . improved quality of health care through a) more uniform, consistent, and proven methods, and b) elimination of proprietary solutions which are too often less than optimum, poorly substantiated, and costly.

James W. Waite, "A Multirate Bank of Digital Bandpass Filters for Acoustic Applications," *Hewlett -Packard Journal,* pp. 75–81, April 1993. Acousticians prefer to see the data distributed in constant percentage bandwidths, usually octave or ⅓ octave bands, since the auditory perception of sound is logarithmically related to frequency and several regulations require such presentation. The FFT has severe limitations for use in acoustics. The output of the FFT has a constant bandwidth distribution rather than a constant percentage bandwidth distribution, that is, the frequency scale is linear rather than logarithmic. The frequency of the lowest band is limited by a lack of resolution at the low-frequency end of the spectrum. An FFT analyzer that claims to match the performance of a traditional bank of analog ⅓-octave bandpass filters must overlap data acquisition and processing, and cannot disregard samples at its analog-to-digital converter at any time. Even in this world of faster processing horsepower, this is a difficult task given the considerations listed above. Filter analyzers are not without their own shortcomings. Constant percentage bandwidths allow only coarse frequency resolution toward the higher end of the acoustic spectrum, making the measurement of discrete tones difficult. Also, at low frequencies, the very narrowband ⅓-octave filters have long impulse responses, resulting in lengthy filter settling times. Wavelet analysis is a promising technology. Wavelets have properties that make them very attractive for the measurement of sound. For the immediate future, however, the world of sound is seen through the poles and zeros of bandpass filters, analog or digital. Digital Signal Processing (DSP) is also used by the acoustics community. Digital filters have for some time replaced the old analog ⅓-octave filter banks, and are available as dedicated real-time frequency analyzers or filter analyzers, as distinguished from FFT spectrum analyzers, dynamic signal analyzers, and others that derive their results from the FFT. The digital filter analyzers are typically composed of a subset of single-purpose filter gate arrays, bit-slice microprocessors, and medium-scale integration DSP multiplier-accumulators. Such dedicated hardware has made it difficult for the digital filter analyzers to perform other signal processing tasks.

What is needed is a new paradigm for the design of instruments for medical care, and, in particular, a new spectrum analyzer without the disadvantages associated with those now commercially available. This, then, is what the invention provides.

NOVELTY OF THE INVENTION

The invention provides for a universal, multipurpose instrument for extending the range of abilities of both the specialist and the primary caregiver. It is to the medical field as the well-known oscilloscope is to the electronic field. Whereas the oscilloscope is based on the cahode ray tube, the invention is based on the spectrum analyzer. The disadvantages previously discussed in regard to spectrum analyzers are overcome by the artificial cochlea of this invention. Said artifical cochlea endeavors to model the functioning of the inner ear.

SUMMARY OF THE INVENTION

The invention automates and generalizes the use of auscultation, a medical procedure in which the caregiver listens to heart and lung sounds by means of a stethoscope. This is accomplished by replacing the ear by a microphone connected to a spectrum analyzer. In the preferred embodiment said spectrum analyzer is the previously mentioned artificial cochlea.

Similarly the invention automates a number of chemical tests, by analyzing the chemical spectra obtained at the output of a mass spectrometer augmented by other means, for instance a chromatograph.

The invention also includes means representative of commercially available hardware and software technology, for instance means for running expert system programs for assisting in the diagnosis of medical conditions and means for communicating by telephone with other specialists or databases.

The special requirement for the use of the invention is that it be operable in bedrooms and other inconvenient locations and that it leave the hands of the caregiver free to minister to his patient(s). Consequently the invention also requires the use of voice-activation and speech synthesis as methods of communication between the caregiver user and the invention. For the same reasons a miniature video terminal is also used which can be worn like a clip-on monocular.

BRIEF DESCRIPTION OF THE DRAWINGS

FIG. 1 illustrates the preferred embodiment of the universal medical instrument of the invention.

DETAILED DESCRIPTION

A careful analysis of the referenced documents will reveal the increasing importance and potential of spectrum analysis in supplementing or even replacing auscultation in medical examinations. It is worth noting the complexity of the computational and other burdens imposed on the various experimenters as a result of trying to overcome the (severe) limitations of existing spectrum analyzers.

The state of the art and limitations of existing methods of obtaining the frequency spectra of sound and waveforms in general have already been covered in detail in the preceding discussions.

The spectrum analyzer is defined in the IEEE Standard Dictionary of Electrical and Electronics Terms as "an instrument generally used to display the power distribution of an incoming signal as a function of frequency."

The historical background and capabilities of the spectrum analyzer of the invention are reflected in the four definitions that follow:

Organic Memory (OM): "a memory that can forget." In the parlance of Artificial Neural Networks (ANNs) each memory location in such a memory is a "neuron" which is connected to a plurality of preceding neurons or inputs, randomly selectable in time via a connection with an associated gain (or weight). As with the classical ANNs the quantity stored in a "neuron" is the (algebraic) sum of the weighted quantities from said previous neurons or inputs. Ulike classical ANNs, however, the OM also causes the quantity stored in a given neuron to decay in (real) time as a function of a corresponding quality factor Q. The need for a sigmoid or other threshold activation function is therefore avoided. For further details, see U.S. Pat. No. 4,809,222, entitled "Associative and Organic Memory Circuits and Methods."

Resonant Processing Unit (RPU): an updated version of the OM used as a recognition engine and described in a later disclosure. See U.S. patent application Ser. No. 07/912,899 filed Jul. 13, 1992.

Artificial Cochlea (AC): RPU programmed to emulate the (presumed) operation of the natural cochlea, the spiral cavity in the internal ear in man and most mammals where pitch discrimination occurs. The natural cochlea is an example of a natural, real-time spectrum analyzer without the problems of the sound spectrograph. The natural cochlea has been said to incorporate the equivalent of a (large) number of individually tuned, narrow bandpass filters operating simultaneously and in parallel. No commercially available spectrum analyzer comes close to the simplicity and suitability of the AC for analyzing sounds in this way.

Biocomputer: for the purposes of the present invention biocomputer 3 of FIG. 1 consists of any computer or grouping of multiprocessing elements connected to one or more spectrum analyzers which in turn are connected to sensors, in this case one or more microphones 13, for interfacing directly with the chest of a patient or another appropriate environment. Said spectrum analyzer(s) can be ACs or any other configuration that performs the necessary functions. Said spectrum analyzers and the associated hardware and software are intended to replace humans as the source of interpreted data. The preferred embodiment of this invention uses an AC and a microphone to replace a human ear and a stethoscope.

The VDH Biocomputer, for the present purpose, is the multiprocessing element described in cross-reference 4 entitled "Multiprocessing Element for Computing Using Exact and Inexact Data," Application Ser. No. 07/912,899 filed Jul. 13, 1992. It uses the RPU as a recognition engine. Said recognition engine can be programmed as a novel neural network and, as has already been mentioned, an AC. In a practical application such as the present invention, it is desirable to use a plurality of said multiprocessing elements and RPUs because of the many tasks and processes that must take place simultaneously. Spectrum analysis, voice activation (see later) and chemical signature identification tasks (see later) can take place in either the same RPU or in a plurality of RPUs, each one of said plurality dedicated to a portion or the totality of a said given task.

The VDH Biocomputer is the embodiment preferred over all other biocomputer means 3 as shown on FIG. 1.

The Artificial Cochlea (AC) is not subject to the limitations of the FFT algorithm: it is not restricted to a linear frequency scale and sound or waveform data can be processed "on the go," i.e., in the order and at the time that they are sampled. Memory requirements are thus lessened and manipulations that interfere with real time data processing avoided. The range and distribution of the frequencies is not limited to what the human ear is capable of. Last but not least, the limitations of analog (hardware) bandpass filtration methods do not apply.

For the purposes of the present disclosure the detailed operation of the AC can be abbreviated as follows: in the AC, (as in the RPU) two main steps occur during the processing of a given data sample obtained from a source ID and with magnitude x: first x is multiplied by a weight W (in this case a coupling factor) and stored in memory at an address A; then data previously stored at said address A is multiplied by a quality factor Q (descriptive of a loss factor in the present case) and added to the contents at said memory address A. (Note that x, W, Q and the contents at address A are algebraic quantities.) When quality factor Q remains unchanged over a number of cycles t, the successive values of a quantity stored in memory address A vary as an exponential function of the form $x*Q^t$.

When the weight factor W varies like the data from source ID, the result is a resonant system where the numerical value of the data in memory location A increases steadily. An analogous situation is observed in physical resonant systems when energy is added "in phase." Hence the name Resonant Processing Unit.

The proper choice of W and Q values makes it possible to simulate or analyze oscillations and transient phenomena in electronic circuits and mechanical assemblies. The value of W is related to the "coupling coefficient" and that of Q to the "quality factor" or "damping coefficient." The Q factor then acts to control selectivity or bandpass, exactly like in a regular electronic or mechanical filter.

One method of implementing the Fourier Transform in the AC consists of assigning, for each frequency of interest, two weight factors W and W' and two memory addresses A and A'. W and W' are sinusoids (for instance, a sine and a cosine function at the given frequency of interest.) A constant quality factor Q is normally used. The first address A is assigned to the component in phase (real axis) and the second address A' is assigned to the quadrature component (imaginary axis.) Thus a phasor (i.e., a vector in two-dimensional space with an amplitude and a phase angle) can be calculated from the values found at memory addresses A and A'.

During a single cycle of operation the following signals referenced to a moment in real time are supplied to the (hardware) circuits of the AC: a sample of the chosen input function (for instance a sound waveform) obtained from a source ID; corresponding quantities descriptive of ID, W, Q; and address A. The final result will be stored in address A at the end of the cycle.

Said final result, and others at other Addresses A can be read simultaneously but independently without interfering with the functioning of the AC by use of dual-porting or other methods of simultaneously accessing the same (neuronal) memory.

The number of samples of the input function(s) needs to be sufficiently high with respect to said frequency of interest in order to guarantee sufficient accuracy and prevent aliasing due to the higher frequency components of the (input) signal being sampled.

It is helpful to visualize the AC as the equivalent of a (large) bank of tuned resonator filters, with each filter independently programmable as to frequency and selectivity. As has already been mentioned before, the limitations of physical analog bandpass filters do not apply. The fact that the choice of available frequencies extends as far above or below the range of natural hearing as desired makes it possible for the AC to analyze waveforms descriptive of blood pressure and lung expansion (i.e., respiration), both of which cannot be heard as a sound by the human ear. This has the potential of yielding additional important information on the functioning of the vascular system (including the heart valves) and the lungs.

The mass spectrometer (see later) also generates a spectrum; but instead of frequencies it identifies chemical elements by their charge-to-mass ratio. Since more than one chemical element can have the same charge-to-mass ratio, it is helpful to use it in conjunction with other means, for instance a chromatograph. Sound and chemical spectra can be fed to a RPU or neural network for further identification with known "spectral signatures."

The concept of "signature" applies to a recognizable grouping of sounds or chemicals without however being able to identify their exact composition in terms of frequencies or compounds. Signatures are usually each associated with a specific object or chemical compound, or said object or compound's condition, state, etc. They are the biological equivalent of a noise, a smell, a taste or a color. The IEEE Standard Dictionary of Electrical and Electronics Terms has its own approach to the concept, and offers the following definition:

signature diagnosis (test, measurement and diagnostic equipment). The examination of signature of an equipment for deviation from known or expected characteristics and consequent determination of the nature and location of malfunctions.

"Libraries" or collections of standard sound or chemical signatures, indicative of well-defined illnesses or conditions, can be compiled for later comparison with the equivalent signatures obtained in the course of medical examinations. By identifying the standard signature that most resembles that obtained in a specific case, an automated, standardized diagnosis may be obtained. Such a diagnosis, coming from a machine must however always be approved by a human since said machine lacks context and acts like an "idiot savant." It could, for instance, confuse a drumbeat with a heartbeat.

The libraries of standard signatures need not be contained in local memory, at least not in their entirety. A network of databases to be remotely accessed by telephone would be easy to establish and operate. The key here is to be able to reduce the amount of information (data bits) that must travel through the communication means. Spectrum analysis reduces a sound or waveform to a short list of frequency, phase and amplitude values and is therefore ideal for the purpose. Spectrum analyzers in effect act as hardware to compute Fourier or possibly other transformations and represent a universal or natural way of "compressing" heartbeat and other signatures. This has already been discussed in the introductory portion of the present disclosure. See, among others, the comments relating to the article entitled "ECG Data Compression Techniques—A Unified Approach," by Jalaleddine et al.

Referring to FIG. 1:

In the preferred embodiment, the invention would be contained in two carrying cases 1 and 6, each approximately 20 inches long, 10 inches wide, and 15 inches high. These maximum dimensions, with some possible modifications, are chosen as optimum because they correspond to what the airlines consider acceptable for "carry-on" luggage.

The invention is designed to be operated while standing on the floor because it must be usable in bedrooms and other confined spaces with no available desk or tabletop space. For this reason also, the invention must be operable without the usual keyboard and video data terminal.

Case 1 contains a biocomputer 5 and case 6 a chemical analyzer 8. Both can run on electrical power 19, which can be from the usual sources (like "house" current—110 Volts 60 Hertz in the U.S.) or from batteries, preferably one or more 12 Volts DC automotive or marine batteries because of their availability anywhere in the world.) Power supplies that can run from a variety of power sources including batteries are well known in the art. Biocomputer 3 is as defined above.

Cases 1 and 6 have lids 2 and 7 with optional carrying handles (not shown on the Figure for clarity.) Inside cases 1 and 6 and under lids 2 and 7 are two shallow storage spaces 5 and 10. Below said storage spaces 5 and 10 are instrument panels 4 and 9 which in turn constitute the top surfaces of biocomputer 3 and chemical analyzer 8.

When it is desired to operate the apparatus of the invention lids 2 and 7 are opened as shown on the Figure and accessories 12 are removed from storage spaces 5 and 10, together with any trays and/or containers that might be used for their storage. The connecting cables and/or tubes of accessories 12 are then connected to apparatus 3 and 8 by plugging attached cable and tube assemblies 25 and 24 into the appropriate sockets/connectors in said instrument panels 4 and 9. As a matter of fact all electrical and other connectors are located on panels 4 and 9 so that the apparatus of cases 1 and 6 can be operated while standing on the floor.

The accessories 12 for biocomputer 3 consist of modified stethoscope 13 and headset 14. Also included in the same storage area 5 are phone patch 16 for connecting to a telephone service 17 (either a regular home/business telephone outlet or other cellular or satellite cellular accessory), one or more power cords 18 (for instance one for AC house current and one for battery power) for connecting to a source of power 19 and an electrical cable 11 for interconnecting biocomputer 3 and chemical analyzer 8.

The accessories 12 connected to chemical analyzer 8 include one or more chemical "heads" 15 for analyzing gases, liquids and solids.

Modified stethoscope 13 is in reality a microphone. Since the frequency response of the complete system comprising microphone 13 and biocomputer 3 can be extended above and below the range of (humanly) audible frequencies, the function of auscultation performed with the aid of stethoscope/microphone 13 can also encompass the inaudible frequencies associated with muscle tremors, respiration rhythms, blood pressure fluctuations and the like. This is useful for diagnosing muscle spasms, vascular, heart valve and other problems not normally amenable to diagnosis by auscultation.

The transducer assembly of microphone 13 can also serve as a means for generating sound or mechanical vibrations or stimuli for the purposes of percussion, a process in which the resonance etc. of the thoracic cavities yields additional useful information. Electrodynamic loudspeakers and piezoelectric transducers are examples of transducers whose function can be reversed, i.e. the same transducer can be used for both "receiving" and "transmitting." Of course, separate transmitting and receiving transducers can also be linked to the same diaphragm, membrane or other means for coupling to the chest, back or other appropriate body surface. This is well understood in the art.

Headset 14 includes one or two earphones 20, a microphone 21 that can be positioned near the mouth of the operator and a miniature video display 22 that is worn like a loupe in front of the operator's (right or left) eye. Said miniature video display 22 can also be retracted out of the way to an alternate position 22A. A plurality of push-buttons 23, mounted on the earphone(s) or in any other convenient location, complete the assembly of headset 14. Miniature video displays are well-known in the art; a typical application is in viewfinders for camcorders. A special method of high-resolution graphics is discussed in the cross-referenced patent U.S. Pat. No. 4,649,506 entitled "Vector Generator Using Interpolative Analog Circuits." Vector methods are particularly suitable for small, (very) high resolution graphic displays, both in monochrome and in color. The color producing means can consist of color shutters as manufactured and sold by Tektronix in Oregon. Said color shutters overcome the resolution problem encountered in small color CRTs using the usual color dot matrices or stripes.

Headset 14 allows the doctor, nurse or other caregiver to give spoken commands to biocomputer 3 via microphone 21 and push-button(s) 23, and receive audio and video information from biocomputer 3 via earphones 20 and miniature video display 22. Biocomputer 3 is also connected to chemical analyzer 8 by means of cable 11. The data generated by chemical analyzer 8 and other means are transmitted to and processed by biocomputer 3 and then presented to the operator as sounds, speech, pictures and text through the intermediary of the previously described means contained in headset 14.

Voice activation and synthesis are now well-known in the art, for instance in voice-controlled VCRs, and voice-synthesis has long been used in reading machines for the blind and the like.

Chemical head(s) 15 are used for inputting organic and inorganic samples to chemical analyzer 8. Chemical analyzer 8 consists of, but is not limited to, a mass spectrometer such as is well known in the art. The quadrupole mass spectrometer described by Ingvar Sodal and George Swanson in one of the referenced documents is a good example of a miniature unit that can be modified for the purpose. Chemical "heads" 15 can be as described by Sodal and Swanson or can be redesigned in any number of ways to accommodate not only gases, but liquids and solids as well by first turning the latter into gases. A number of suitable methods are known in the art and include vaporizing, burning, etc. Further refinements for resolving the ambiguity caused by elements with the same charge to mass ratio include, but are not limited to, chromatography. Chromatography is also a well-known art.

Hardware and software for communicating by standard, cellular and even satellite cellular telephone are now commercially available and are already being used to access remotely located individuals, computers, clinics, databanks and administration centers. Instead of the telephone, which is a means of communicating by wires, other suitable means of communications can also be used, including, but not limited to, transmitters and receivers that communicate by means of sound, RF, light or any other form of radiant energy. "Ham radio" is an example of a method of long distance communication by means of RF short-wave electromagnetic radiation. Its proponents are found throughout the world and one of their traditions has been to be ready to maintain long distance communications during emergencies.

Fuzzy logic and the design of "user-friendly" software, including the design of so-called "expert systems" and tutorial programs in general is within the purview of present-day programmers and will enable the biocomputer to assist in diagnosis and interact with all of the above resources in an efficient manner.

LIST OF REFERENCE NUMERALS
FIG. 1

| | |
|---|---|
| 1 | Case 1 |
| 2 | Lid of Case 1 |
| 3 | Biocomputer |
| 4 | Instrument Panel of Biocomputer |
| 5 | Storage Space of Case 1 |
| 6 | Case 6 |
| 7 | Lid of Case 6 |
| 8 | Chemical Analyzer |
| 9 | Instrument Panel of Chemical Analyzer |
| 10 | Storage Space of Case 6 |
| 11 | Cable Connection, output of 8 to inputs of 3 |
| 12 | Accessories |
| 13 | Microphone (stethoscope) |
| 14 | Headset |
| 15 | Chemical Head/Organic and Inorganic Sample Input Means |
| 16 | Telephone patch cord |
| 17 | Telephone Outlet |
| 18 | Power Cable |
| 19 | Power Source |
| 20 | Earphone |
| 21 | Microphone (voice activation input) |
| 22 | Miniature Video Display |
| 22A | Alternate Position of Miniature Video Display |
| 23 | Push-button |
| 24 | Cable + Tubes; Chemical Analyzer input connection |
| 25 | Cable; biocomputer accessory input connection |

I claim:

1. A universal medical instrument for replacing humans as the source of interpreted data and for identifying sound and chemical signatures equivalent to noises, smells, and tastes indicative of health conditions comprising:

an artificial cochlea for complementing the ear of a caregiver by providing continuous, real-time, spectral analysis of body sounds and vibrations connected to a source of sounds and vibrations through the appropriate sensor in a stethoscope of the caregiver, a chemical mass spectrometer for complementing the chemical senses of the caregiver by providing continuous, real-time, spectral analysis of biological samples connected to a source of organic and inorganic samples through appropriate chemical head(s), a biocomputer connected to said artificial cochlea and said chemical mass spectrometer for processing their outputs, and interfacing with the caregiver by means of appropriate audio and video readouts.

2. A method of augmenting the capabilities of a caregiver at a location and during a time that he or she ministers to a patient comprising the following method steps:

obtaining organic and inorganic material samples from a patient's body and deriving the chemical spectra of said organic and inorganic samples;

obtaining sounds and vibrations from said patient's body and deriving the frequency spectra of said sounds and vibrations;

comparing said chemical spectra and said frequency spectra to equivalent, stored reference spectra indicative of medical conditions by means of an apparatus to provide a diagnosis;

communicating with said apparatus by means of voice message to obtain said diagnosis and instructions and help.

* * * * *